United States Patent
Favero et al.

(10) Patent No.: US 12,091,480 B2
(45) Date of Patent: Sep. 17, 2024

(54) METHOD FOR PRODUCING 2-DIMETHYLAMINOETHYL (METH)ACRYLATE

(71) Applicant: SNF GROUP, Andrezieux Boutheon (FR)

(72) Inventors: Cédrick Favero, Andrezieux Boutheon (FR); Johann Kieffer, Andrezieux Boutheon (FR); Jing Ling, Taixing (CN)

(73) Assignee: SNF GROUP, Andrezieux Boutheon (FR)

( * ) Notice: Subject to any disclaimer, the term of this patent is extended or adjusted under 35 U.S.C. 154(b) by 970 days.

(21) Appl. No.: 17/041,746

(22) PCT Filed: Apr. 12, 2018

(86) PCT No.: PCT/CN2018/082774
§ 371 (c)(1),
(2) Date: Sep. 25, 2020

(87) PCT Pub. No.: WO2019/196048
PCT Pub. Date: Oct. 17, 2019

(65) Prior Publication Data
US 2021/0114969 A1    Apr. 22, 2021

(51) Int. Cl.
*C08F 220/34* (2006.01)
*C07C 213/08* (2006.01)
*C07C 213/10* (2006.01)
*C07C 219/08* (2006.01)

(52) U.S. Cl.
CPC .......... *C08F 220/34* (2013.01); *C07C 213/08* (2013.01); *C07C 213/10* (2013.01); *C07C 219/08* (2013.01)

(58) Field of Classification Search
CPC ... C08F 220/34; C07C 213/08; C07C 213/10; C07C 219/08; Y02P 20/584
See application file for complete search history.

(56) References Cited

U.S. PATENT DOCUMENTS

| | | | |
|---|---|---|---|
| 7,071,351 B2 | 7/2006 | Schmitt et al. | |
| 8,067,637 B2 | 11/2011 | Priebe | |
| 2010/0068156 A1* | 3/2010 | Kim | A61Q 19/10 |
| | | | 526/263 |
| 2012/0123148 A1 | 5/2012 | Paul et al. | |

FOREIGN PATENT DOCUMENTS

| | | |
|---|---|---|
| CN | 1437574 A | 8/2003 |
| CN | 101516934 A | 8/2009 |
| CN | 102448605 A | 5/2012 |
| CN | 105330556 A | 2/2016 |
| WO | 2009/087804 A1 | 7/2009 |
| WO | 2011/157645 A2 | 12/2011 |

OTHER PUBLICATIONS

International Search Report (and English translation) and Written Opinion of the International Searching Authority for International Application No. PCT/CN2018/082774 mailed on Nov. 29, 2018.

* cited by examiner

*Primary Examiner* — Catherine S Branch
(74) *Attorney, Agent, or Firm* — Heslin Rothenberg Farley & Mesiti P.C.

(57) ABSTRACT

Process for the production of 2-dimethylaminoethyl (meth)acrylate in multiple stage batch reactions involving the recycling of the catalyst (DBTO) in subsequent reaction, the addition a certain amount of fresh catalyst to the recycled catalyst, the use of said catalysts in the subsequent reaction, and wherein the volume decrease due to azeotropic distillation is compensate in order to keep the volume constant in the reactor during the reaction by the continuous addition of a composition comprising methyl(meth)acrylate and dimethylaminoethanol.

18 Claims, No Drawings

METHOD FOR PRODUCING 2-DIMETHYLAMINOETHYL (METH)ACRYLATE

CROSS REFERENCE TO RELATED APPLICATIONS

This application is a national stage filing under section 371 of International Application No. PCT/CN2018/082774 filed on Apr. 12, 2018, and published on Oct. 17, 2019 as WO 2019/196048. The entire contents of WO 2019/196048 are hereby incorporated herein by reference.

TECHNICAL FIELDS

The invention relates to a process for the production of 2-dimethylaminoethyl (meth)acrylate, also called DMAE (M)A or (M)ADAME®.

BACKGROUND TECHNIQUE 2-dimethylaminoethyl (meth)acrylate monomer is generally quaternized, for example with methyl chloride, dialkylsulfate or benzylchloride and then polymerized to produce cationic polymers. These polymers are used in many industries, such as water treatment, paper making, home and personal care, oil & gas recovery.

It is well-known to catalyze transesterification reaction with organo-tin compounds. Amongst (meth)acrylic esters of interest, 2-dimethylaminoethyl (meth)acrylate is obtained by transesterification of alkyl(meth)acrylate and dimethylaminoethanol with tin oxide derivatives as catalyst, for example dibutyltin oxide (DBTO). The catalyst's role is to displace the equilibrium to produce more 2-dimethylaminoethyl (meth)acrylate and reduce the impurity formation The alkyl(meth)acrylate can be methyl(meth)acrylate, ethyl(meth)acrylate, propyl(meth)acrylate, butyl(meth)acrylate, 2-ethylhexyl (meth)acrylate. Methyl (meth)acrylate is generally preferred.

It is also known that other metal alkoxides can be used as transesterification catalyst, such as aluminium (III) isopropoxide, or tetra alkoxide titanate (IV), such as described in U.S. Pat. No. 8,067,637 or CN 105330556. Acetylacetonate derivatives are also used as catalyst, for example metal complex of zirconium, aluminium, zinc, iron acetylacetonate such as described in U.S. Pat. No. 7,071,351 or WO 2001/157645. DBTO is a particularly advantageous catalyst because it is very active at low dosage, can be recycled multiple times and minimize the impurity formations, on the opposite of the titanate derivative catalyst which require stoechiometric amount of the catalysts related to starting materials.

Despite this advantage, DBTO tends to be deactivated upon recycling and it is necessary to replace it regularly which is costly, and generates toxic waste which is difficult to manage and to treat.

When DBTO starts to be deactivated, the reaction product contains more impurities. Typically, in the reaction between methyl(meth)acrylate and dimethylaminoethanol with DBTO as catalyst, there are impurities created as by-products which decrease the quality of 2-dimethylaminoethyl (meth)acrylate. These impurities are the Michael adducts of methanol or dimethylaminoethanol which have reacted with methyl(meth)acrylate, dimethylaminoethyl (meth)acryl ate, or (meth)acrylic acid.

To limit the formation of impurities such as Michael adducts formed with low molecular weight alcohols (methanol), it is known to make the reaction in a solvent. This allows the elimination of low molecular weight alcohols during a continuous azeotropic distillation. The drawback of this method is a continuous decrease of the volume in the reactor rendering less productive the process.

At the end of the reaction, the catalyst is separated from the reaction mixture and recycled if its catalyst activity is enough to limit the impurity formations.

Generally, in the first reaction, fresh DBTO is used as catalyst. After the reaction, 100% of DBTO recovered from the first reaction is recycled in the second reaction. After the second reaction, 100% of DBTO recovered from the second reaction is recycled in the third reaction. But the DBTO recovered in the third reaction has not a sufficient catalytic activity to be used in a fourth reaction. In other terms, if this DBTO is used in a fourth reaction, the quality of the 2-dimethylaminoethyl (meth)acrylate is low because it will contain a lot of impurities.

SUMMARY

The problem to solve in this invention is to improve the efficiency of the process of production of 2-dimethylaminoethyl (meth)acrylate and the quality of the monomer obtained.

It has been surprisingly found that this can be done by a more efficient use of the volume of the reactor, and a more efficient use of the catalyst. The present invention is based on two principles. The first one is the continuous addition of a composition comprising methyl(meth)acrylate, dimethylaminoethanol to compensate the volume decrease due to the azeotropic distillation and removal of the low molecular weight alcohol. The second one is the addition of a portion of fresh DBTO, in addition to the recycled DBTO, in at least a subsequent batch reaction.

The present invention provides a process for the production of 2-dimethylaminoethyl (meth)acrylate comprising at least two sequential batch reactions wherein in each batch reaction, methyl(meth)acrylate, dimethylaminoethanol, dibutyltin oxide as catalyst, and a solvent are added as initial charge in an agitated reactor equipped with a distillation column, wherein an azeotropic distillation is made continuously during the reaction, wherein the volume decrease due to said azeotropic distillation is compensated in order to keep the volume constant in the reactor during the reaction by the continuous addition of a composition comprising methyl(meth)acrylate and dimethylaminoethanol, said composition may also comprise dibutyltin oxide, said process comprising:

A first batch reaction wherein the dibutyltin oxide used as catalyst is a fresh dibutyltin oxide;

A separation step wherein the dibutyltin oxide from the first batch reaction is recovered from the reaction mixture of the first batch reaction, and that constitutes a recycled dibutyltin oxide;

At least a second batch reaction wherein at least 65% by weight of the recycled dibutyltin oxide is used with fresh dibutyltin oxide as catalyst of the second batch reaction:

Wherein the amount of fresh dibutyltin oxide is comprised between 0.1% by weight and 35% by weight based on the recycled dibutyltin oxide from the first batch reaction, wherein the mass proportion of recycled dibutyltin oxide and fresh dibutyltin oxide, added in the initial charge is comprised between 220/1 and 80/20, wherein the mass proportion of recycled dibutyltin oxide and fresh dibutyltin oxide, in the composition continuously added to compensate the azeotropic distillation in the case of comprising dibutyltin oxide, is comprised between 100/0 and 0/100.

By definition, fresh dibutyltin oxide means that the dibutyltin oxide is used for the first time in a reaction. In other terms, the fresh dibutyltin oxide has not been recovered from a previous reaction of production of 2-dimethylaminoethyl (meth)acrylate. The term new dibutyltin oxide is also used in the present invention, and have the same meaning as fresh dibutyltin oxide.

In a preferred embodiment, the process of the invention comprises a least one subsequent batch reaction wherein at least 65% by weight of the recycled dibutyltin oxide from the previous reaction is used with fresh dibutyltin oxide as catalyst of said reaction:

Wherein the amount of fresh dibutyltin oxide is comprised between 0.1% by weight and 35% by weight based on the recycled dibutyltin oxide from the previous reaction, wherein the mass proportion of recycled dibutyltin oxide from the previous reaction and fresh dibutyltin oxide, added in the initial charge is comprised between 220/1 and 80/20, wherein the mass proportion of recycled dibutyltin oxide from the previous reaction and fresh dibutyltin oxide, in the composition continuously added to compensate the azeotropic distillation in the case of comprising dibutyltin oxide, is comprised between 100/0 and 0/100.

The process of the invention is a multiple stage batch reactions involving the recycling of the catalyst (DBTO) in subsequent reaction, and the addition a certain amount of fresh or new catalyst to the recycled catalyst, and the use of said catalysts in the subsequent reaction.

The continuous addition of a composition comprising methyl(meth)acrylate and dimethylaminoethanol during the reaction allows the use of the maximum volume of the reactor which is advantageous in terms of productivity. This composition may also comprise dibutyltin oxide, which is preferred.

The combination of this maximum use of the reactor volume, the recycling of the DBTO, and the fresh addition of DBTO in the specific ratio of the invention allows the improvement of the efficiency of the process of production of 2-dimethylaminoethyl (meth)acrylate and the improvement of the quality of this monomer. 2-dimethylaminoethyl (meth)acrylate is better in quality because it contains less impurities. The monomer quality is also more consistent upon subsequent batch as the catalyst activity is maintained constant at an optimum concentration for all batch. Another advantage of the process of the invention is the decrease of the overall catalyst consumption per batch, and so the decrease of overall waste generated per batch.

In a preferred embodiment of the invention, the process of the invention comprises a total of at least 3, preferably 4, more preferably 5, even more preferably 6, even more preferably 7, even more preferably 8, even more preferably 9, even more preferably 10, and up to 20 batch reactions in which the recycled dibutyltin oxide from the previous reaction is used in combination with fresh dibutyltin oxide as catalyst according to the invention.

In other term, it means that after the first reaction of the process of the invention which involves the only use of fresh catalyst, the process of the invention comprises at least 2, preferably 3, more preferably 4, even more preferably 5, even more preferably 6, even more preferably 7, even more preferably 8, even more preferably 9, and up to 19 batch reactions in which the recycled dibutyltin oxide from the previous reaction is used in combination with fresh dibutyltin oxide as catalyst according to the invention.

The reactions according to the invention are made in an agitated reactor equipped with a distillation column and a mean to increase the temperature. Generally, the solvent, methyl(meth)acrylate, dimethylaminoethanol and the dibutyltin oxide (DBTO) are added in the reactor. As known in the art, the reaction is induced with a temperature increase. Methanol produced from the reaction is continuously evaporated with some solvent and some (meth)acrylic ester, and are directed into the distillation column. The recovered solvent is preferably recycled after separation from the alcohol and the (meth)acrylic ester.

The solvent used in the process of the invention is preferably an inert solvent, and is typically an alkane from C6 to C12, linear, cyclic or branched. Preferred solvent is hexane which form an azeotropic mixture with low molecular weight alcohol, especially with methanol.

According to the invention the volume decrease due to the evaporation of these products is continuously compensated by the continuous addition of an equivalent volume of a composition comprising methyl(meth)acrylate and dimethylaminoethanol. In a preferred embodiment, this composition also comprises dibutyltin oxide and solvent. In a more preferred embodiment, the composition is the same as the composition initially added in the reactor before the beginning of the reaction.

The skilled man of the art knows how to conduct the reaction and could refer to the document US 2012/0123148. The process of the invention does not require specific additional manner to make the reaction to obtain 2-dimethylaminoethyl (meth)acrylate by transesterification of methyl (meth)acrylate and dimethylaminoethanol with dibutyltin oxide (DBTO) as catalyst. The chemicals proportion, the temperature and other parameters of the reaction are well-known.

At the end of each batch reaction, 2-dimethylaminoethyl (meth)acrylate is recovered from the reaction mixture, and purified, generally by distillation. The DBTO is also recovered and recycled as described in the invention. The skilled man of the art knows how to conduct these processes.

In a preferred embodiment, the reactions of the process of the invention are made in the same reactor, but can also be made in different reactors.

In a preferred embodiment, in the second and/or in the subsequent batch reaction according to the invention, at least 80% by weight, preferably at least 85%, more preferably at least 90% of the recycled dibutyltin oxide recovered from the previous reaction is used with fresh dibutyltin oxide as catalyst of the subsequent reaction.

In a preferred embodiment, the amount of fresh dibutyltin oxide in each of the subsequent reaction is comprised between 0.1% by weight and 20% by weight based on the recycled dibutyltin oxide, preferably between 0.5% and 15% by weight, even more preferably between 0.5% and 10% by weight.

In a preferred embodiment, the mass ratio of recycled dibutyltin oxide and fresh dibutyltin oxide, added in the initial charge of each of the subsequent reaction is comprised between 97/3 and 85/15, preferably between 95/5 and 87/13. Even more preferably, this mass ratio is 90/10.

In a preferred embodiment, in each subsequent reaction, the mass ratio of recycled dibutyltin oxide and fresh dibutyltin oxide, in the composition continuously added to compensate the azeotropic distillation in order to keep the volume constant in the reactor in the case of comprising dibutyltin oxide, is comprised between 95/5 and 5/95, preferably between 90/10 and 10/90.

In a preferred embodiment, the mass ratio of recycled dibutyltin oxide and fresh dibutyltin oxide is the same between the dibutyltin oxide added in the initial charge of each of the subsequent reaction, and the composition continuously added to compensate the azeotropic distillation. In this case, a preferred mass ratio is preferably comprised between 97/3 and 85/15, preferably between 95/5 and 87/13, even more preferably 90/10, even more preferably 99/1.

The present invention also provides the 2-dimethylaminoethyl (meth)acrylate obtained according to the process of the invention. The monomer 2-dimethylaminoethyl (meth) acrylate obtained has a better quality because it contains less impurities. The monomer quality is also improved because it is more homogenous batch after batch compared to the process in which no fresh addition of catalyst is made, and in which the volume decrease is not compensated (there is a significant declining quality batch after batch). This is because the process of the invention allows a more uniform action of the catalyst batch after batch.

The present invention also provides the 2-dimethylaminoethyl (meth)acrylate mixture recovered after a separation step from the reaction mixture obtained according to the process of the invention. Said 2-dimethylaminoethyl (meth) acrylate contains less impurities and is better in quality.

The present invention also provides a quaternized version of 2-dimethylaminoethyl (meth)acrylate of the invention. The quaternization is made for example with dimethylsulfate, diethylsulfate, benzyl chloride or methylchloride, or a mixture thereof, and preferably with methylchloride to convert the tertiary amine to a quaternary ammonium.

The present invention also provides a polymer made with the quaternized version of 2-dimethylaminoethyl (meth) acrylate of the invention. Any polymerization process may be used such as gel polymerization, liquid or emulsion polymerization. Any form of the polymer may be obtained, such as a powder, an emulsion, a dispersion, solution. The polymer of the invention is preferably water soluble, but also may be water swellable.

Other monomers may be used in combination with the quaternized version of 2-dimethylaminoethyl (meth)acrylate to produce the polymer of the invention. These monomers may be selected in the following list:
Non-ionic monomers: acrylamide, methacrylamide, N,N-dimethylacrylamide, N,N-diethylacrylamide, N-vinylpyrrolidone, N-vinylformamide, N-vinyl imidazole, the methacrylates of polyethylene glycol, diacetoneacrylamide, N-isopropylacrylamide, 2-hydroxyethyl acrylate, 2,3-dihydroxypropyl acrylate, 2-hydroxyethyl methacrylate, 2,3-dihydroxypropyl methacrylate,N-tert-butylacrylamide,
Anionic monomers: acrylic acid, 2-acrylamido-2-methyl-propane sulfonic acid (ATBS), methacrylic acid, itaconic acid, maleic acid, ally sulfonate, non-salified, partially or completely salified,
Cationic monomers: diallyldimethylammonium chloride (DADMAC), acrylamido dialkylaminopropyl, methacrylamido dialkylaminopropyl, and their acidified or quaternized salts,
Structure agent: polyethylenically unsaturated monomers (having at least two unsaturated functional groups), such as, for example, vinyl, allyl, acrylic and epoxy functional groups, and there may be mentioned, for example, methylenebisacrylamide (MBA), triallylamine, tetrallylammonium chloride or by macroinitiators such as the polyperoxides, polyazo compounds and transfer polyagents such as polymercaptan polymers.

The polymer according to the invention is not limited in term of molecular weight. The polymer has preferably an average molecular weight by weight comprised between 5.000 and 100.000 g/mol, or an average molecular weight by weight comprised between 100.000 and 1.000.000 g/mol, or an average molecular weight by weight comprised between 1.000.000 and 30 million g/mol. The average molecular weight by weight is measured by Gel Permeation Chromatography (GPC).

The present invention also provides the use of the polymer of the invention in water treatment, sludge dewatering, papermaking process, agriculture, cosmetic and detergency composition, textile process, oil and gas recovery process such as enhanced oil recovery, fracturing, mining operation such as tailings treatment.

Embodiments

The present invention will now be illustrated in greater details by way of following examples.

EXAMPLES

Common to All Examples: $1^{St}$ Batch with Fresh DBTO

A 12 liters jacketed reactor is equipped with an agitator, a packed column with 10 theoretical plates, a reflux condenser and a decanter. 950 g of hexane, 6520 g of methyl acrylate and 3380 g of dimethylaminoethanol are loaded to the reactor.

121 g of fresh DBTO is loaded. To avoid polymerization, 10 g of phenotiazine is also loaded into the reactor.

The reaction mixture is heated to 80° C. with an external heater. During the reaction, a continuous addition of raw materials and catalyst is added to the reactor to compensate the volume which decreases. The continuous feed is composed of 105.2 g of hexane, 722 g of methylacrylate, 374 g of dimethylaminoethanol.

After 30 min, the DBTO is active and azeotropic mixture of hexane/methanol/methylacrylate is generated into the distillation column. The distillate is mixed with water and settled. Organic phase is sent back to the reactor.

After 10 h of heating, 1210 g of methanol is recovered, the reaction is finished.

Reaction mixture is then transferred to a distillation kettle equipped with rectification tower. 5160 g of 2-dimethylaminoethylacrylate is recovered as distillate, which corresponds to a yield of 95%.

The 2-dimethylaminoethylacrylate is analyzed by GC-FID and its purity is 99.9%

After the distillation, DBTO remains in the kettle as a high boiling compound and is used in the following examples as recycled DBTO:

Examples 1 to 5:

In the 12 liters reactor described previously, same quantities of methylacrylate, dimethylaminoethanol and hexane as those of the above first batch reaction are loaded to the reactor. 100% weight of the recycled DBTO from previous batch is re-used in subsequent batch, which corresponds to 121 g.

108.9g of recycled DBTO is initially loaded into the reactor, which corresponds to 90% weight of the recycled DBTO from previous batch. In addition, a quantity of fresh DBTO is initially loaded into the reactor, the% by weight related to the 108.9 g of recycled DBTO is mentioned in table 1.

During the reaction, a continuous addition of raw materials and catalyst is added to the reactor to compensate the volume which decreases. The continuous feed is composed of 105.2g of hexane, 722 g of methylacrylate, 374 g of dimethylaminoethanol and 12.1g of recycled DBTO, which corresponds to 10% weight of the recycled DBTO from previous batch. In addition, a quantity of fresh DBTO is loaded, the % weight related to the 12.1g of recycled DBTO is mentioned in table 1.

After the end of reaction and purification with rectification tower, the final dimethylaminoethylacrylate is analyzed by GC-FID. The recycled DBTO is considered not enough active when the purity of final dimethylaminoethylacrylate drops below 99.8%.

Counter Example

Same procedure is applied than in examples 1 to 5, except there is no amount of fresh DBTO added to the reactor (only recycled DBTO), and there is no continuous feed of raw material and catalyst during the reaction to compensate the volume lost by azeotropic distillation.

Results are summarized in Tables 1-2.

batch. In consequence, there is an increase of the maximum number of batches to produce satisfactory monomer quality. The production is also increased thanks to the use of the complete volume of the reactor all along the reaction. Globally, the process is significantly improved compared to the existing process.

The invention claimed is:

1. A process for the production of 2-dimethylaminoethyl (meth)acrylate comprising a total of at least two and up to twenty sequential batch reactions wherein in each batch reaction, methyl(meth)acrylate, dimethylaminoethanol, dibutyltin oxide as catalyst, and a solvent are added as initial charge in an agitated reactor equipped with a distillation column, wherein an azeotropic distillation is made continuously during the reaction, wherein the volume decrease due to said azeotropic distillation is compensated in order to keep the volume constant in the reactor during the reaction by the continuous addition of a composition comprising methyl(meth)acrylate and dimethylaminoethanol, said composition may also comprise dibutyltin oxide said process comprising:
   a first batch reaction wherein the dibutyltin oxide used as catalyst is a fresh dibutyltin oxide;
   a separation step wherein the dibutyltin oxide from the first batch reaction is recovered from the reaction mixture of the first batch reaction, and that constitutes a recycled dibutyltin oxide;
   at least a second batch reaction wherein at least 65% by weight of the recycled dibutyltin oxide is used with fresh dibutyltin oxide as catalyst of the second batch reaction:

TABLE 1

| | Amount of recycled DBTO used in subsequent reaction | % recycled DBTO used in subsequent reaction based on the recycled DBTO from the previous reaction | Amount of recycled DBTO used in the initial load | % recycled DBTO used in the initial load based of recycled DBTO from the previous reaction | Amount of recycled DBTO used in the composition continuously added | % recycled DBTO used in the composition continuously added based of recycled DBTO from the previous reaction |
|---|---|---|---|---|---|---|
| CEx | 121 g | 100% | 108.9 g | 90% | 12.1 g | 10% |
| Ex1 | 121 g | 100% | 108.9 g | 90% | 12.1 g | 10% |
| Ex2 | 121 g | 100% | 108.9 g | 90% | 12.1 g | 10% |
| Ex3 | 121 g | 100% | 108.9 g | 90% | 12.1 g | 10% |
| Ex4 | 121 g | 100% | 108.9 g | 90% | 12.1 g | 10% |
| Ex5 | 121 g | 100% | 108.9 g | 90% | 12.1 g | 10% |

TABLE 2

| | Amount of fresh DBTO used in the initial load | Mass Proportion of recycled DBTO and fresh DBTO in the initial charge | Amount of fresh DBTO used in the composition continuously added | Mass Proportion of recycled DBTO and fresh DBTO used in the composition continuously added | Total amount of fresh DBTO | Total % of fresh DBTO based on the recycled DBTO from the previous reaction | Max number of batches to have satisfactory monomer quality | DBTO Waste (g/batch) |
|---|---|---|---|---|---|---|---|---|
| CEx | 0 g | Non Applicable | 0 g | Non Applicable | 0 g | 0% | 3 | 40.3 |
| Ex1 | 0.545 g | 200/1 | 0.06 g | 200/1 | 0.605 g | 0.5% | 4 | 24.7 |
| Ex2 | 1.089 g | 100/1 | 0.121 g | 100/1 | 1.21 g | 1% | 4 | 25.2 |
| Ex3 | 3.267 g | 33.3/1 | 0.363 g | 33.3/1 | 3.63 g | 3% | 5 | 23.37 |
| Ex4 | 5.445 g | 20/1 | 0.605 g | 20/1 | 6.05 g | 5% | 5 | 25.73 |
| Ex5 | 10.89 g | 10/1 | 1.21 g | 10/1 | 12.1 g | 10% | 6 | 30.62 |

DBTO Waste: total fresh DBTO quantity used during the total of batches divided per this number of batches.

The results demonstrate that the process according to the invention allows a more efficient use of the catalyst thanks to a significant decrease of the overall catalyst consumption per batch, and so the decrease of overall waste generated per wherein the amount of fresh dibutyltin oxide is comprised between 0.1% by weight and 35% by weight based on the recycled dibutyltin oxide from the first batch reaction, wherein the mass proportion of recycled dibutyltin oxide and fresh dibutyltin oxide, added in the initial charge is comprised between 220/1 and 80/20, and wherein the mass proportion of recycled dibutyltin oxide and fresh dibutyltin oxide is between 100/0 and 0/100, in the composition continuously added to compensate the azeotropic distillation, when said composition comprises dibutyltin oxide;

wherein in each batch reaction, the recycled dibutyltin oxide from the previous reaction is used in combination with fresh dibutyltin oxide as catalyst, and wherein the solvent is an alkane from C6 to C12, linear, cyclic or branched.

2. The process according to claim 1 wherein the process comprises at least one subsequent batch reaction wherein at least 65% by weight of the recycled dibutyltin oxide from the previous reaction is used with fresh dibutyltin oxide as catalyst of said reaction:

wherein the amount of fresh dibutyltin oxide is comprised between 0.1% by weight and 35% by weight based on the recycled dibutyltin oxide from the previous reaction, wherein the mass proportion of recycled dibutyltin oxide from the previous reaction and fresh dibutyltin oxide, added in the initial charge is comprised between 220/1 and 80/20, and wherein the mass proportion of recycled dibutyltin oxide from the previous reaction and fresh dibutyltin oxide is between 100/0 and 0/100, in the composition continuously added to compensate the azeotropic distillation, when said composition comprises dibutyltin oxide.

3. The process according to claim 1, wherein the sequential batch reactions of the process are made in the same reactor.

4. The process according to claim 1, wherein the composition comprising methyl(meth)acrylate and dimethylaminoethanol that is continuously added during the reaction to compensate the volume decrease due to the azeotropic distillation comprises methyl(meth)acrylate, dimethylaminoethanol, dibutyltin oxide and solvent.

5. The process according to claim 1, wherein the composition comprising methyl(meth)acrylate and dimethylaminoethanol that is continuously added during the reaction to compensate the volume decrease due to the azeotropic distillation is the same as the composition initially added in the reactor before the beginning of the reaction.

6. The process according to claim 1, wherein in the second and/or in the subsequent batch reaction, at least 80% by weight of the recycled dibutyltin oxide recovered from the previous reaction is used with fresh dibutyltin oxide as catalyst of the subsequent reaction.

7. The process according to claim 1, wherein the amount of fresh dibutyltin oxide in each of the subsequent reactions is between 0.1% by weight and 20% by weight based on the recycled dibutyltin oxide.

8. The process according to claim 1, wherein in each subsequent batch reaction, the mass ratio of recycled dibutyltin oxide and fresh dibutyltin oxide, added in the initial charge of each of the subsequent reaction is between 97/3 and 85/15.

9. The process according to claim 1, wherein the mass ratio of recycled dibutyltin oxide and fresh dibutyltin oxide, in the composition continuously added to compensate the azeotropic distillation in order to keep the volume constant in the reactor in case of comprising dibutyltin oxide, is between 95/5 and 5/95.

10. A process for the production of a polymer of 2-dimethylaminoethyl (meth)acrylate, comprising:

performing the process according to claim 1, thereby producing 2-dimethylaminoethyl (meth)acrylate; and polymerizing said 2-dimethylaminoethyl (meth)acrylate to obtain the polymer.

11. The process according to claim 1, further comprising performing a separation step to recover a 2-dimethylaminoethyl (meth)acrylate mixture from reaction mixture obtained according to the process of claim 1.

12. The process according to claim 1, wherein the process produces a quaternized version of 2-dimethylaminoethyl (meth)acrylate or a quaternized version of a 2-dimethylaminoethyl (meth)acrylate mixture.

13. The process according to claim 10, wherein the polymer is made with a quaternized version of 2-dimethylaminoethyl (meth)acrylate.

14. The process according to claim 10, wherein the polymer is obtained by the polymerization of a quaternized version of 2-dimethylaminoethyl (meth)acrylate and at least one monomer selected from the following list:

non-ionic monomers: acrylamide, methacrylamide, N,N-dimethylacrylamide, N,N-diethylacrylamide, N-vinylpyrrolidone, N-vinylformamide, N-vinyl imidazole, the methacrylates of polyethylene glycol, diacetoneacrylamide, N-isopropylacrylamide, 2-hydroxyethyl acrylate, 2,3-dihydroxypropyl acrylate, 2-hydroxyethyl methacrylate, 2,3-dihydroxypropyl methacrylate, N-tert-butylacrylamide, anionic monomers: acrylic acid, 2-acrylamido-2-methylpropane sulfonic acid (ATBS), methacrylic acid, itaconic acid, maleic acid, ally sulfonate, non-salified, partially or completely salified, cationic monomers: diallyldimethylammonium chloride (DADMAC), acrylamido dialkylaminopropyl, methacrylamido dialkylaminopropyl, and their acidified or quaternized salts, structure agent: polyethylenically unsaturated monomers having at least two unsaturated functional groups, selected from the group consisting of: vinyl, allyl, acrylic, epoxy functional groups, methylenebisacrylamide (MBA), triallylamine, tetrallylammonium chloride; or by macroinitiators such as the polyperoxides, polyazo compounds and transfer polyagents such as polymercaptan polymers.

15. The process according to claim 10, further comprising adding the polymer to an aqueous solution in a method for water treatment, sludge dewatering, papermaking process, agriculture, cosmetic and detergency composition, textile process, oil and gas recovery process, fracturing, or mining operation.

16. The process according to claim 1, wherein:

the process comprises a total of at least 10 and up to 20 batch reactions in which in each batch reaction, the recycled dibutyltin oxide from the previous reaction is used in combination with fresh dibutyltin oxide as catalyst according claim 1;

in the second and/or in the subsequent batch reaction , at least 90% by weight of the recycled dibutyltin oxide recovered from the previous reaction is used with fresh dibutyltin oxide as catalyst of the subsequent reaction;

in each subsequent batch reaction, the mass ratio of recycled dibutyltin oxide and fresh dibutyltin oxide, added in the initial charge of each of the subsequent reaction is comprised between 95/5 and 87/13; and the mass ratio of recycled dibutyltin oxide and fresh dibutyltin oxide, in the composition continuously added to compensate the azeotropic distillation in order to keep the volume constant in the reactor in case of comprising dibutyltin oxide, is comprised between 90/10 and 10/90.

17. The process according to claim 2, wherein:

the process comprises a total of at least 3, and up to 20 batch reactions in which in each batch reaction, the recycled dibutyltin oxide from the previous reaction is used in combination with fresh dibutyltin oxide as catalyst;

the solvent is an alkane from C6 to C12, linear, cyclic or branched; and the sequential batch reactions of the process are made in the same reactor.

18. The process according to claim 17, wherein the composition comprising methyl(meth)acrylate and dimethylaminoethanol that is continuously added during the reaction to compensate the volume decrease due to the azeotropic distillation comprises methyl(meth)acrylate, dimethylaminoethanol, dibutyltin oxide and solvent.

* * * * *